United States Patent [19]

Kivlighan, Jr.

[11] Patent Number: 5,348,473
[45] Date of Patent: Sep. 20, 1994

[54] MEDICAL TOOL

[76] Inventor: Michael F. Kivlighan, Jr., 1116 Twelfth St., Waynesboro, Va. 22980

[21] Appl. No.: 18,396

[22] Filed: Feb. 17, 1993

[51] Int. Cl.⁵ .......................... A61C 1/10; A61C 3/00; A61C 1/12
[52] U.S. Cl. ................................. 433/114; 433/130; 433/133
[58] Field of Search ................ 433/114, 125, 126, 130, 433/131, 133, 105

[56] References Cited

U.S. PATENT DOCUMENTS

| | | | |
|---|---|---|---|
| 186,504 | 1/1877 | Starr | 433/133 |
| 381,196 | 4/1888 | Winn | 433/133 X |
| 623,469 | 4/1899 | Hailer | 433/130 |
| 794,006 | 7/1905 | Gossling | . |
| 794,007 | 7/1905 | Gossling | . |
| 1,183,535 | 5/1916 | Chayes | 433/130 X |
| 1,379,880 | 5/1921 | Seaborn | 433/130 |
| 1,678,097 | 7/1928 | Andersen | . |
| 1,824,398 | 9/1931 | Feischhacker | 433/130 X |
| 1,982,336 | 11/1934 | Wiseman | . |
| 2,183,415 | 12/1939 | Thommies | 433/133 X |
| 2,400,912 | 5/1946 | Britt et al. | . |
| 2,738,528 | 3/1956 | Fridge, Sr. | . |
| 3,163,934 | 1/1965 | Wiseman | 32/27 |
| 3,411,212 | 11/1968 | Staunt | 32/27 |
| 3,478,433 | 11/1969 | Richmond | 32/59 |
| 3,574,374 | 4/1971 | Keller et al. | 32/26 X |
| 3,621,577 | 11/1971 | Spinello | 32/58 |
| 3,675,330 | 7/1972 | Drapen et al. | 32/59 |
| 3,707,042 | 12/1972 | Talaga | 32/27 |
| 3,727,313 | 4/1973 | Graham | 32/27 |
| 3,727,315 | 4/1973 | Spinello | 32/59 |
| 3,740,853 | 6/1973 | Brahler | 32/59 |
| 3,769,707 | 11/1973 | Condon | 32/27 |
| 3,977,084 | 8/1976 | Sloan | 32/59 |
| 3,987,550 | 10/1976 | Danne et al. | 32/59 |
| 4,021,917 | 5/1977 | Nakanishi | 32/27 |
| 4,053,983 | 10/1977 | Flatland | 32/27 |
| 4,123,845 | 11/1978 | Fattaleh | 32/59 |
| 4,182,041 | 1/1980 | Girard | 433/115 |
| 4,185,388 | 1/1980 | Jarby | 433/125 |
| 4,253,832 | 3/1981 | Bailey | 433/115 |
| 4,259,071 | 3/1981 | Warden et al. | 433/166 |
| 4,266,933 | 5/1981 | Warden et al. | 433/82 |
| 4,286,951 | 9/1981 | Leonard | 433/126 |
| 4,295,829 | 10/1981 | Martinelli et al. | 433/130 X |
| 4,310,310 | 1/1982 | Bailey | 433/126 |
| 4,365,956 | 12/1982 | Bailey | 433/115 |
| 4,406,621 | 9/1983 | Bailey | 433/126 |
| 4,447,208 | 5/1984 | Kawai | 433/166 |
| 4,449,932 | 5/1984 | Lustig | 433/126 |
| 4,475,889 | 10/1984 | Garcia et al. | 433/114 X |
| 4,486,175 | 12/1984 | Fisher et al. | 433/104 |
| 4,544,356 | 10/1985 | Gardella et al. | 433/122 |
| 4,604,058 | 8/1986 | Fisher et al. | 433/127 |
| 5,020,995 | 6/1991 | Levy | 433/215 |
| 5,028,233 | 7/1991 | Witherby | 433/125 |
| 5,040,978 | 8/1991 | Falcon et al. | 433/125 |
| 5,062,796 | 11/1991 | Rosenberg | 433/82 |
| 5,120,220 | 6/1992 | Butler | 433/125 |

FOREIGN PATENT DOCUMENTS

| | | | |
|---|---|---|---|
| 219142 | 5/1957 | Australia | 433/130 |
| 70986 | 8/1915 | Fed. Rep. of Germany | 433/114 |
| 629763 | 5/1936 | Fed. Rep. of Germany | 433/133 |
| 902336 | 4/1945 | France | 433/125 |

*Primary Examiner*—Gene Mancene
*Assistant Examiner*—Nicholas D. Lucchesi
*Attorney, Agent, or Firm*—Hoffman, Wasson & Gitler

[57] ABSTRACT

A medical tool such as a prophy angle is provided having primarily plastic parts to make disposing more economical. A portion of the drive shaft is made of metal to eliminate detrimental deformation. The housing is made of two plastic halves which snap-fit together and have projecting portions which surround a pair of oversized plastic beveled gears. A prophy cup having a locking projection is provided so that the locking projection fits into locking cavity on a stud of the tool. Vanes are disposed on the inside of the cup and have a step-like configuration to aid in retaining polishing paste in the cup.

3 Claims, 6 Drawing Sheets

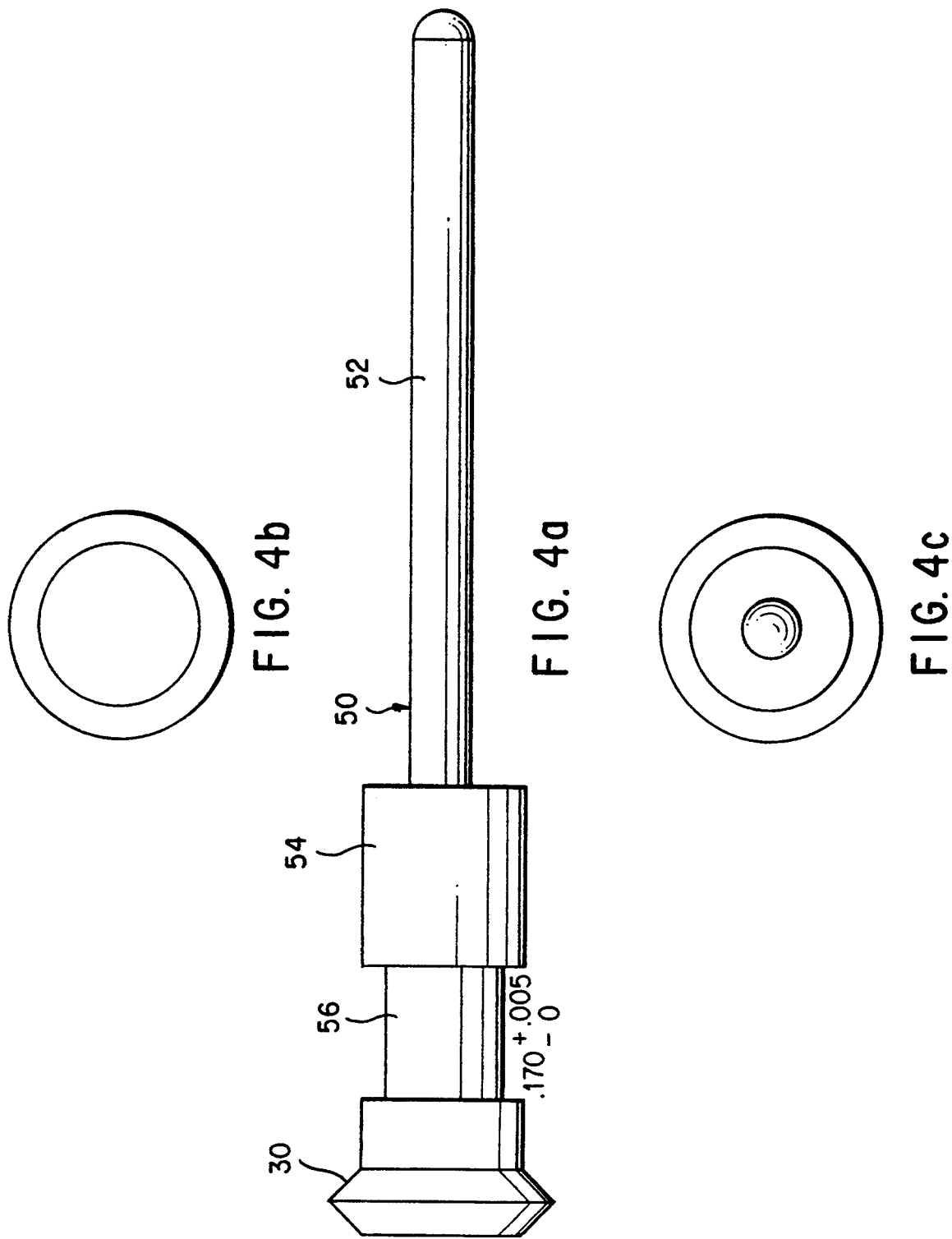

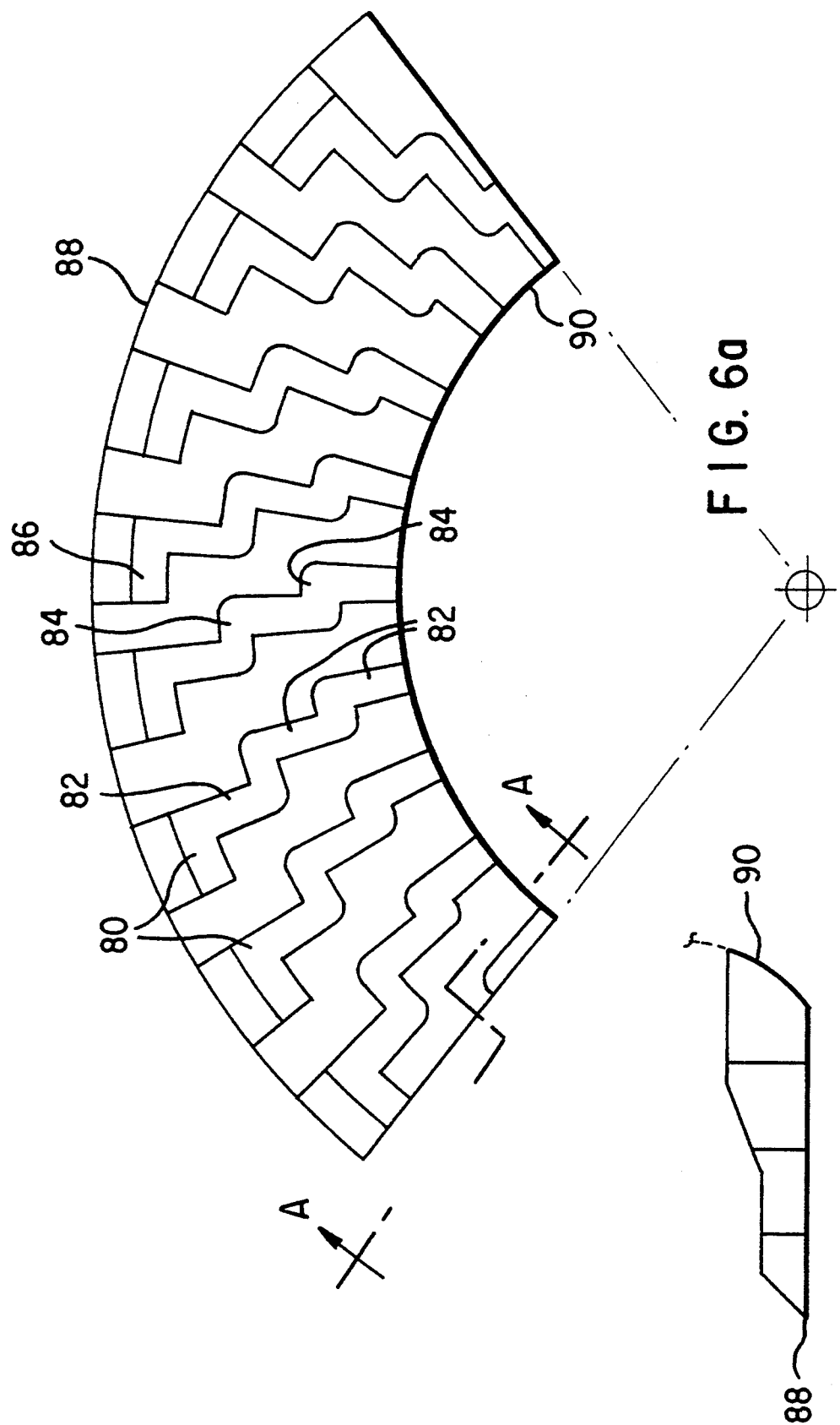

MEDICAL TOOL

BACKGROUND OF THE INVENTION

The present invention pertains to a medical tool such as a dental tool, and in particular to a disposable dental tool, made primarily from plastic and easy to assemble. The invention includes a polishing cup designed to keep polishing paste in the cup during the polishing operation. The dental tool connects to the cup to positively drive the cup, while still allowing use with ordinary polishing cups. The housing of the invention is designed to enclose a pair of gears in a manner similar to common prophy angles, and yet allows for larger sized gears by having a housing which wraps around the gears to provide protrusions at the location of the gears so that gears having a greater diameter than the diameter of the main body housing can be inserted inside.

Medical tools such as Prophy angle dental tools are either disposable or non-disposable. The non-disposable tools comprised primarily of metal parts which are designed for repeated use and require sterilization between uses. Due to the risk of infection and the cost of sterilizing tools after each use, disposable tools are desirable. Disposal of metal tools, however, is not economical. Consequently, plastic prophy angles have been developed which are less expensive than metal ones, and thus can be disposed of economically.

While making parts of the device from plastic reduces the cost, there are some inherent disadvantages to the use of plastic. First, deformation of the plastic is a much greater problem than it was with metal, where it was virtually nonexistent over the life of the tool. When a plastic prophy angle device is connected to a drive motor, the connecting clamp tends to deform the plastic shaft, and thus hinder or impede the operation of the instrument. Second, while the gears of the prophy angle can be made from plastic, such gears tend to wear out much more rapidly than metal gears, and are less accurate and more prone to slippage. Furthermore, plastic gears cannot transmit as much torque as metal gears.

Conventional prophy cups have a recess at one end for receiving a nub or protrusion. The prophy cup is made from an elastic material so that it can deform to accommodate the nub. In a conventional prophy angle tool, slippage can occur between the cup and the nub. To eliminate this slippage, one solution has been to provide a flange of substantially two dimensions projecting outwardly from the end of the nub, and a corresponding groove at the bottom of the recess to accommodate the flange in a manner similar to a screwdriver and a screw head. While such design will reduce the slippage, the modified nub cannot accommodate conventional prophy cups which do not have the screw head formation at the bottom of the recess.

Another problem with prophy cups is the tendency of paste in the prophy cup to migrate outward out of the cup during operation of the tool, thus splattering the patient, doctor, and their surroundings and reducing the effectiveness of the polishing.

In view of the foregoing, it is an object of the present invention to provide a disposable prophy angle dental tool which is made primarily of plastic components, yet eliminates deformation during attachment to the motor portion of the device.

Another object of the present invention is to provide a disposable prophy angle dental tool which has primarily plastic components and can be simply and easily constructed.

Another object of the present invention is to provide a prophy angle dental tool having a housing which permits the use of larger diameter gears, such as beveled gears.

Yet another object of the present invention is to provide a prophy angle dental tool which allows for the attachment of a positive drive prophy cup, but still allows for use with conventional prophy cups.

Another object of the present invention is to provide a prophy angle dental tool which has a specific rib formation on the inside of the cup to reduce the splattering of paste out of the cup during operation of the dental tool.

Yet another object of the present invention is to provide a dental tool which evenly distributes paste along the inner surface of the cup wall during operation of the dental tool.

BRIEF DESCRIPTION OF THE DRAWINGS

The foregoing and other objects of the present invention will be obvious to one of ordinary skill in the art, in view of the following detailed description of the preferred embodiments in connection with the accompanying drawings in which:

FIGS. 4a, 4b, and 4c are a side view and end view a side view of the drive shaft of the present invention shown as attached to the plastic part including one of the plastic gears;

FIG. 5b is a plane view of the bottom of the prophy cup shown in FIG. 5a;

FIG. 6a is a view of a rib configuration from the inside of the prophy cup shown in an unfolded form; and FIG. 6b is a side view of the rib configuration shown in FIG. 6a, taken along line A—A.

DETAILED DESCRIPTION OF THE PREFERRED EMBODIMENT

Figure 1:
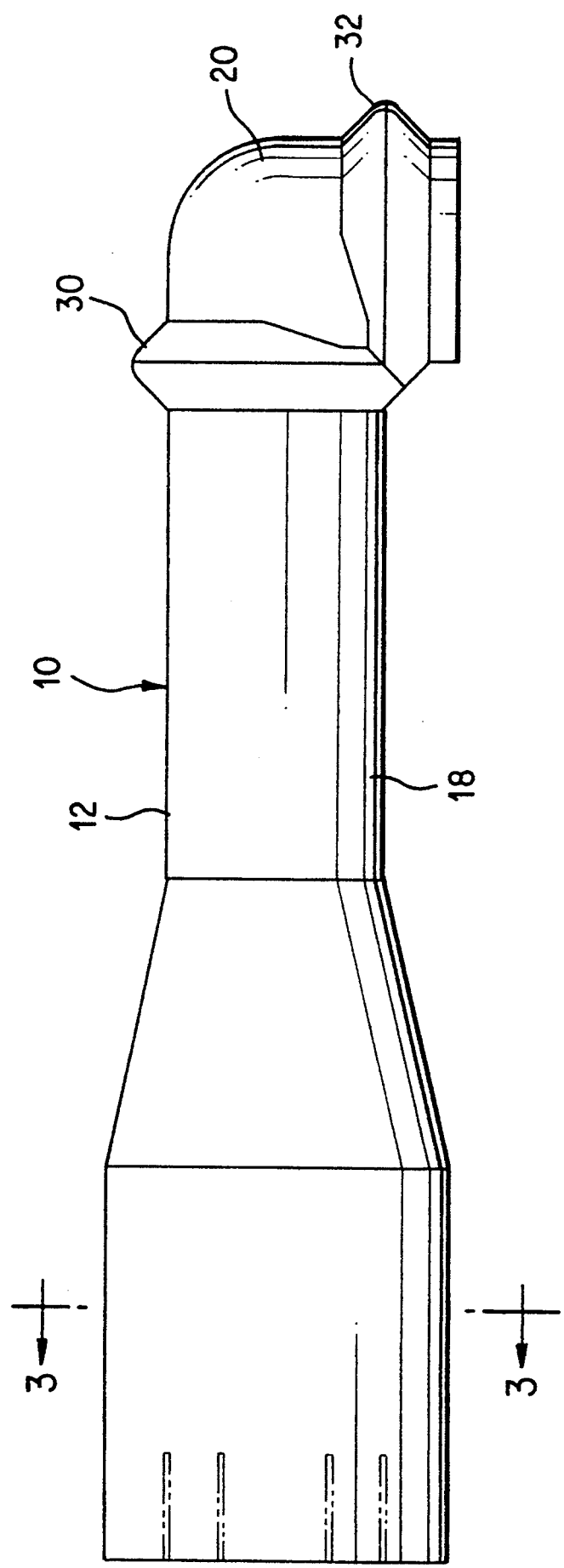
FIG. 1 is a side view of the prophy angle dental tool housing, showing the outside of the tool housing.
Figure 2:
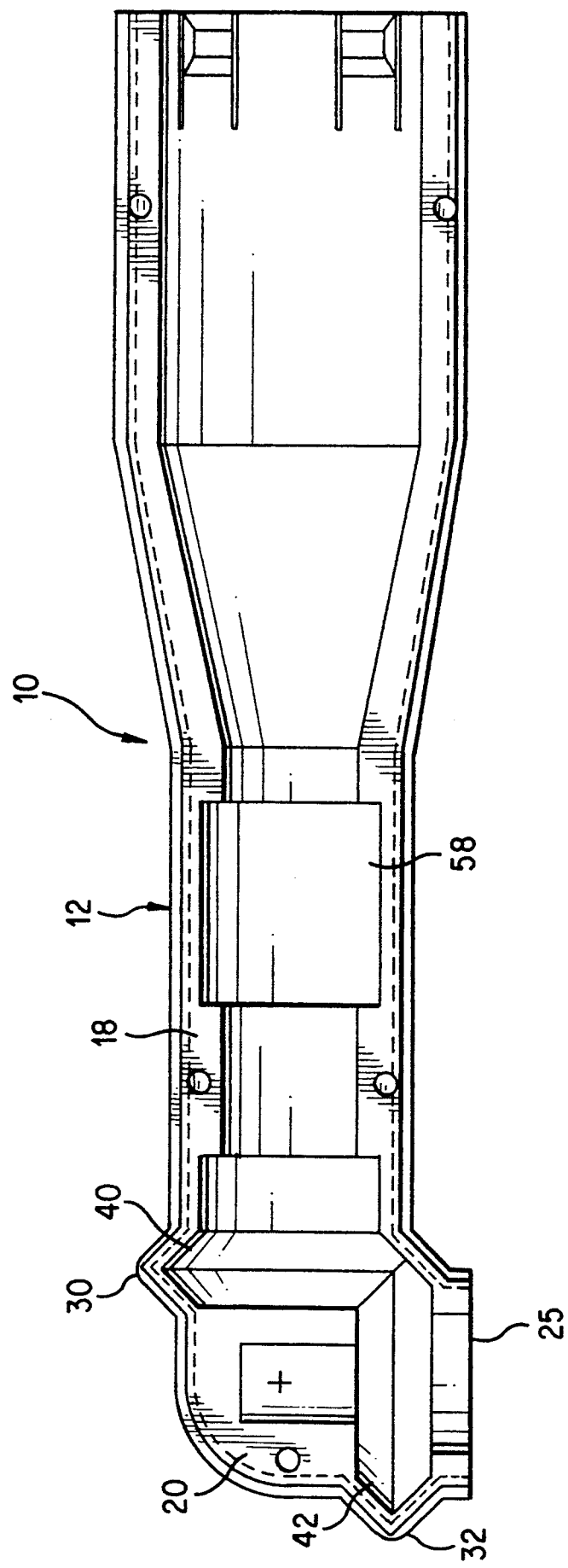
FIG. 2 is a side view of the inside of the housing.
Figure 3:
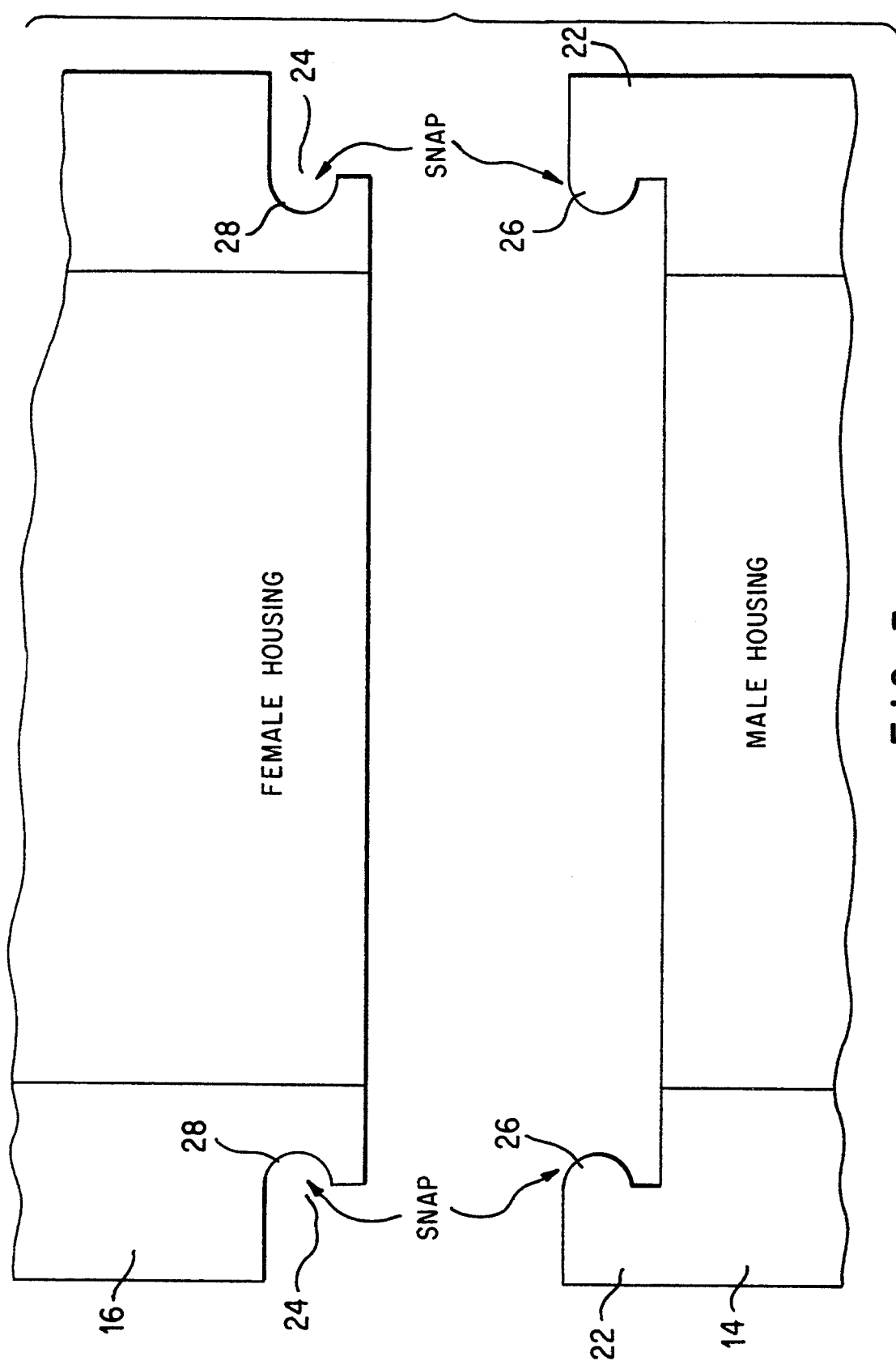
FIG. 3 is an end view of the two halves of the housing showing the snap attachment.

Referring to FIGS. 1-3, the tool 10 of the present invention includes a housing 12 made up of left and right hand housing portions 14 and 16, respectively. Each housing portion 14 and 16 includes an elongated semicircular shaped handle portion 18 and a semicircular head portion 20 meeting at approximately 90 degrees thereto. The housing portions 14 and 16 are made from molded plastic, and are designed so that when the two halves are united, they form a substantially cylindrical passageway to contain various parts to be described later.

Although the left and right housing portions 14 and 16 can be connected in a variety of manners, the preferred manner of connection is shown in FIG. 3. FIG. 3 is a partial cross-sectional view taken along line 3—3 in FIG. 1, and shows the connecting means for connecting the left and right housing portions 14 and 16. Upper and lower flanges 22 project from the upper and lower edges of the left-hand housing 14. The right hand housing 16 has a pair of projecting ridges 24, one formed on each of the upper and lower edges, corresponding to locking cavities 28 formed in the flanges 22 on the left-hand housing 14. A locking ridge 26 projects inwardly and transversely from each of the flanges 22 on the left-hand housing 14. Thus, the locking ridges 26 project inwardly towards the center of the left-hand housing portion 14. Cavities 28 run the length of the housing portion 14, and project approximately transversely from the flanges 22 of the housing 14, and toward the center of the semicircular left-hand housing portion 14. Since both the left and right hand housing portions 14 and 16 are made from plastic, they will return to their original shapes after being subjected to minor deformation forces. Thus, the left and right hand housing portions 14 and 16 are connected by pushing them toward one another as shown in FIG. 3, so that the ridges 24 on the right-hand housing portion 16 project into the cavities 28 of the right-hand housing portion 14, forcing the locking ridges 24 into the locking cavities 28, to maintain the two portions 14 and 16 in their locked position.

Referring to FIGS. 1-2 in the preferred embodiment, the elongated cylindrical handle portion 18 of the housing 12 meets the head portion 20 at an angle of approximately 90°. Other angles may be adopted as long as the internal gears mesh. At the point of merger of these two portions 18 and 20, there is a drive gear protrusion 30. Furthermore, a driven gear protrusion 32 is provided near the working open end 25 of the head portion 20. In the preferred embodiment, the drive gear protrusion 30 and the driven gear protrusion 32 meet one another at substantially 90° to one another. FIG. 2 shows the drive gear cavity 40 and driven gear cavity 42 inside the housing 12 where it is evident that the drive gear cavity 40 and driven gear cavity 42 have inner diameters greater than the inner diameters of the adjacent housing portion 18 and head portion 20.

For dental tools with gears having diameters less than the diameters of their housings and heads, the size of such gears is significantly less, resulting in further difficulties. One of the objects of the present invention is to provide a disposable dental tool which is made of plastic to reduce the expense of such disposability. Making the gears from plastic is one way to reduce the costs. Plastic gears, however, have drawbacks. For example, the plastic gears wear out much more quickly than metal gears. Furthermore, since the gears are smaller in the prior art, the size of the gear teeth is significantly smaller too. If the gears are made from plastic, such small gears are prone to a significant deformation, reducing the effectiveness of the tool, and increasing the wear of the gears. Consequently, since the gears of the tool 10 of the present invention are made from plastic, in order to reduce deformation, the diameter of the gears is increased. To this end, the present invention provides for the drive gear protrusion 30 and the driven gear protrusion 32 as shown in FIGS. 1-2 to permit the use of gears (not shown) which have larger diameters than the inner diameters of the adjacent housing portion 18 and head portion 20 of the dental tool 10.

Moreover, larger gears are capable of transmitting greater torque to the polishing cup or workpiece. Larger diameter gears can accommodate more teeth while having a greater contact area between the two gears. More teeth allows for better meshing of the gears, all of which reduces stress on the gears and provides smoother operation of the tool.

The drive shaft 50 of the tool 10, shown in FIGS. 4a, 4b, and 4c, extends through the housing 12. The drive gear 30 is mounted at one end. As stated previously, it is advantageous to make the components from plastic when developing a disposable tool. However, as was the case with the gears, manufacturing components from plastic can be a drawback. The plastic housing discussed above is designed to be attached to a metal power section. In such a connection, the drive shaft 50 will be gripped by a portion or clamp (not shown) of the power section, to drive the workpiece. If the drive shaft 50 is made from plastic, the gripping force applied from the power section can deform the drive shaft 50 inhibiting proper operation of the tool 10, or alternatively, preventing such operation completely. Consequently, the drive shaft 50 of the present invention is partially made from metal to eliminate such deformation. While the entire drive shaft 50 could be made from metal, making as much of the dental tool 10 which is to be disposed of, from plastic, reduces the costs relating to such disposable tools. Thus, as shown in FIG. 4, a drive shaft 50 is provided in which the shaft 52 is formed from metal, while the hub portion 54 to which the shaft 52 is connected is formed from plastic. The hub portion 54 has a diameter significantly larger than the drive shaft 52, and larger than the diameter of a connecting portion 56 connecting the hub portion 54 to the drive gear 30. Both the hub portion 54 and the connecting portion 56 are made from plastic.

The drive shaft 52 and hub portion 54 may be connected in any one of a variety of manners, such as through screw threading, glue, or gnarlling of the metal shaft.

Figure 5A:
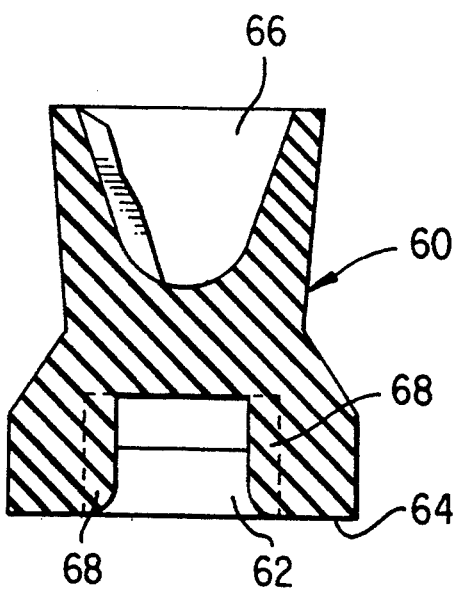
FIG. 5a is a side cross-sectional view of the prophy cup according to the present invention.
Figure 5B:
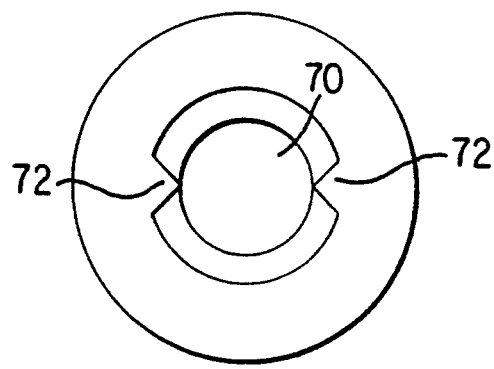
Figure 5C:
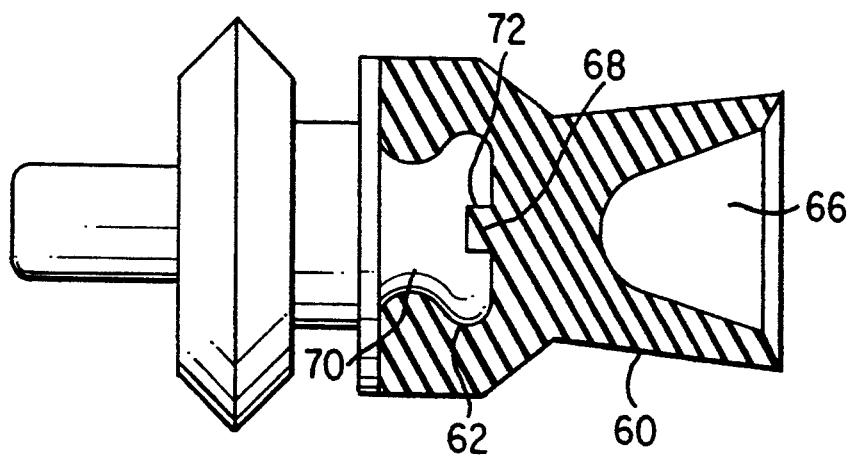
FIG. 5c is a side cross-sectional view of the prophy cup shown in FIG. 5a and an attached stud.

Shown in FIGS. 5a, 5b & 5c is a prophy cup 60 according to the present invention. Prophy cups have long been used to polish teeth. Conventional prophy cups are made from a rubber like substance, and are provided with a pocket or cavity at one end for engagement with a stud having an enlarged head on the working end of the tool. The pocket is designed to fit over the stud for a tight fit to secure the cup against the exposed part of the dental tool. Such a connection, however, is subject to slippage between the prophy cup and the stud. One method of reducing such slippage has been to provide an enlarged flat head portion projecting up from the stud, which fits in a correspondingly shaped recess in a polishing element. However, by such a design, it is impossible to use conventional prophy cups on the dental tool.

The prophy cup 60 shown in FIGS. 5a, 5b & 5c has an improved positive drive design, which reduces the amount of slippage between the prophy cup 60 and the stud 70 projecting from the working end 25 of the head portion 20, and is still capable of being utilized with conventional prophy cups.

More particularly, as shown in FIG. 5a, the prophy cup 60 of the present invention includes a stud recess 62 in the bottom portion 64 of the prophy cup 60 opposite the polishing portion 66. As shown in FIG. 5c, an indentation 72 is located on stud 70. The prophy cup 60, which is made from rubber or a similar substance, has a projection 68 projecting inwardly into the stud recess 62. Consequently, when the prophy cup 60 of the present invention is fitted over the stud 70, the projection 68 locks into indentation 72. When the cup rotates, the projection 68 interacts with the indentation 72, to reduce slippage between the cup 60 and the stud 70. Since the stud 70 has indentation 72 extending into it instead of having a projection extending outwardly, conventional prophy cups can still be utilized on top of the stud 70. If the improved prophy cups are not available, the dental tool 10 of the present invention is still useful in combination with existing prophy cups. While only one indentation and projection are shown, and while they are located on the top of stud and bottom of the cup, the numbers and location can be modified and still achieve improved positive drive.

Finally, a vane pattern of the prophy cup 60 of the present invention is shown in FIGS. 6a & 6b. In the exploded view shown in FIG. 6a, the prophy cup 60 is provided with a series of vanes 80 in the polishing portion 66 of the cup 60. Vanes 80 reduce the tendency of polishing materials to fly out of the cup during operation. Each vane 80 is designed to have a step-like configuration, which includes radial segments 82 and annular segments 84. The number of steps can vary, and in the illustrated embodiment, three steps are provided. The radial segments 82 are oriented so that they project along a radius of the cup 60 outwardly from the center thereof. Each annular segment 84 extends from a radial segment 82 in the same direction as the direction of rotation of the cup 60. The outermost annular segment 86 is a transverse end portion, and has a length greater than the annular segments 84 located radially inward therefrom. As shown in FIG. 6b, the extent to which the vanes 80 project into the cup increases as one moves from the outer edge 88 of the cup 60 to the inner edge 90 of the cup 60. This increase along with the stepwise configuration of the vanes 60, causes polishing material to accumulate in the junctures of each of the radial segments 82 and annular segments 84. Furthermore, the paste will tend to be spread more evenly throughout the length of the cup 60, thus providing polishing material along more of the surface of the tooth being polished. In previous cups, if the paste was not flying out of the cup, it was accumulating only at the bottom of the cup, and therefore was not available to polish the tooth along the entire length of the cup. The vanes 80 project further into the cup 60 near the bottom of the cup 60 to hold the pumice or polishing paste in place. The portion of the cup 60 near the outer edge 88 deforms during use as it is pressed against teeth. Such flaring of the cup would be inhibited by the vanes 80 if the extent they project into the cup 60 is uniform. Therefore, the portions of the vanes 80 near the outer edge project into the cup 60 less than the portions near the inner edge 90. The outer edge 88 can thereby get under the gingiva and be more effective.

Although the present invention has been described in connection with the preferred embodiment, it will be appreciated by those skilled in the art that additions, substitutions, modifications, and deletions, not specifically set forth may be made without departing from the spirit and scope of the invention as defined in the appended claims.

What is claimed is:

1. A medical tool, comprising:
   a housing including an elongated cylindrical body and a substantially cylindrical head portion transverse to an axis of said cylindrical body;
   a drive gear; and
   a driven gear;
   wherein at least one of said drive gear and said driven gear have a diameter greater than an inside diameter of one of said cylindrical body and said head portion, respectively,
   said drive gear being disposed in said cylindrical body and said driven gear being disposed in said substantially cylindrical head portion, and
   further comprising protrusions extending from said elongated cylindrical body and said cylindrical head portion, said protrusions accommodating said drive gear and said driven gear, respectively.

2. A medical tool as recited in claim 1, wherein said drive gear and said driven gear have beveled faces, and said protrusions conform to the shape of these beveled faces.

3. A medical tool as recited in claim 1, wherein at least one of said cylindrical body and said head portion have a protrusion surrounding portions of at least one of said drive gear and said driven gear, respectively, extending beyond said cylindrical body and said head portion.

* * * * *